United States Patent [19]

Ichikawa et al.

[11] Patent Number: 5,432,071

[45] Date of Patent: Jul. 11, 1995

[54] VARIANT E1 PROTEIN GENE FOR PYRUVATE DEHYDROGENASE COMPLEX AND VARIANT E1 PROTEIN OF PYRUVATE DEHYDROGENASE COMPLEX

[75] Inventors: Toshio Ichikawa; Yasuji Koyama; Hideko Otake; Eiichi Nakano, all of Noda, Japan

[73] Assignee: Kikkoman Corporation, Noda, Japan

[21] Appl. No.: 215,709

[22] Filed: Mar. 22, 1994

[30] Foreign Application Priority Data

Apr. 8, 1993 [JP] Japan .................................. 4-082130

[51] Int. Cl.$^6$ ...................... C12N 9/04; C12N 15/53; C12N 15/70
[52] U.S. Cl. ................................. 435/190; 435/69.1; 435/189; 435/252.33; 435/320.1; 536/23.2; 935/10; 935/14; 935/29; 935/73
[58] Field of Search ............ 435/191, 189, 190, 320.1, 435/69.1, 252.3, 252.33, ; 536/23.2

*Primary Examiner*—Robert A. Wax
*Assistant Examiner*—William W. Moore
*Attorney, Agent, or Firm*—Finnegan, Henderson, Farabow, Garrett & Dunner

[57] ABSTRACT

The present invention relates to variant $E_1$ protein of pyruvate dehydrogenase complex of high activity in which arginine at the 146-position is replaced by proline in the amino acid sequence of wild-type $E_1$ protein of pyruvate dehydrogenase complex, a gene coding for said variant $E_1$ protein, a novel recombinant DNA comprising said variant $E_1$ protein-encoding gene inserted in a vector DNA, and a process for producing variant $E_1$ protein by said recombinant DNA. The present invention provides the variant $E_1$ protein of pyruvate dehydrogenase complex of high activity.

4 Claims, No Drawings

VARIANT E1 PROTEIN GENE FOR PYRUVATE DEHYDROGENASE COMPLEX AND VARIANT E1 PROTEIN OF PYRUVATE DEHYDROGENASE COMPLEX

FIELD OF THE INVENTION

The present invention relates to variant $E_1$ protein in a pyruvate dehydrogenase complex, a gene coding for the $E_1$ protein, a recombinant DNA containing the gene, and a process for producing the $E_1$ protein.

BACKGROUND OF THE INVENTION

A pyruvate dehydrogenase complex, utilized for quantitative determination of pyruvate acid, etc., finds various utilities because pyruvic acid is an intermediate for many reaction systems.

The pyruvate dehydrogenase complex as a whole is an enzyme that catalyzes oxidative decarboxylation of pyruvic acid in the presence of TPP (thiamin pyrophosphate) or lipoamide as a coenzyme, as follows:

Pyruvic
acid+$NAD^+$+CoA→Acetyl-CoA+$CO_2$+-
NADH+$H^+$

This enzyme is actually an enzyme complex of molecular weight of several millions consisting of 3 types of enzyme proteins ($E_1$, $E_2$ and $E_3$), each of which catalyzes one of the following reaction steps. Out of the complex, the present invention relates to the E1 protein (pyruvate dehydrogenase).

Pyruvic
acid+$E_1$-TPP→$E_1$-TPP-CHOH-$CH_3$+$CO_2$

{$E_1$: pyruvate dehydrogenase}
$E_1$-TPP-CHOH-$CH_3$+$E_2$-$LipS_2$+CoA→$E_1$-
TPP+acetyl-CoA+$E_2$-Lip(SH)$_2$ {$E_2$: dihydrolipoamide acetyltransferase}
$E_3$ $E_2$-Lip(SH)$_2$+$NAD^+$⇌$E_2$-$LipS_2$-
+NADH+$H^+$ {$E_3$: lipoamide dehydrogenase}
{in the above reactions, TPP is thiamin pyrophosphate, $LipS_2$ is lipoic acid, and Lip(SH)$_2$ is dihydrolipoic acid.}

As $E_1$ protein of wild-type pyruvate dehydrogenase complex and a nucleotide sequence coding therefor, those derived from E. coli K12 are known (see Eur. J. Biochem., Vol. 133, No. 1, pp. 155-162 (1983), and Biochem. J., Vol. 287, pp. 611-619, particularly p. 616, right column, lines 19-31 (1992)).

The object of the present invention is to provide a large amount of variant $E_1$ protein of higher activity by means of genetic engineering.

In the process of cloning an $E_1$ protein gene derived from the wild-type E. coli strain 1100 by the PCR technique, the present inventors have obtained variant $E_1$ protein in which one amino acid is replaced by another amino acid, and they have unexpectedly found that said variant $E_1$ protein possesses an extremely higher activity compared with the wild-type $E_1$ protein of known sequence.

SUMMARY OF THE INVENTION

The present invention relates to a gene coding for the variant $E_1$ protein of pyruvate dehydrogenase complex wherein arginine at the 146-position is replaced by proline in the amino acid sequence of the wild-type $E_1$ protein of pyruvate dehydrogenase complex.

In addition, the present invention relates to a recombinant DNA comprising said gene coding for the variant $E_1$ protein of pyruvate dehydrogenase complex inserted into a vector DNA.

Furthermore, the present invention relates to a process for producing said $E_1$ protein by culturing a microorganism of genus Escherichia containing said recombinant DNA and then recovering the variant $E_1$ protein of the pyruvate dehydrogenase complex from the culture.

Finally, the present invention relates to the thus obtained variant $E_1$ protein itself of the pyruvate dehydrogenase complex.

DETAILED DESCRIPTION OF THE INVENTION

Hereinafter, the present invention is described in detail.

In the present invention, the variant $E_1$ protein of high activity with one amino acid replaced is obtainable in a step of cloning the $E_1$ protein gene by the PCR (Polymerase Chain Reaction) technique. Therefore, a genomic DNA containing the wild type $E_1$ protein gene serving as a template in the PCR must be prepared.

The genomic DNA serving as a template is not particularly limited insofar as it contains the $E_1$ protein gene of the wild-type pyruvate dehydrogenase complex, which is preferably a genomic DNA derived from E. coli including e.g. E. coli strain K12, E. coli strain 1100 (obtained from Max Plank Institute, Heidelberg, Germany).

For example, the genomic DNA of E. coli strain 1100 is prepared by collecting said microorganisms by centrifugation etc. and then treating them according to a method described e.g. in Current Protocols in Molecular Biology, Vol. 1, Section 2 (1987).

For cloning of the $E_1$ protein gene from the genomic DNA, the PCR technique can be used because the nucleotide sequence of said gene has already been revealed in European Journal of Biochemistry (Vol. 133, pp. 155-162 (1983)). That is, N- and C-terminal single-stranded DNA primers are prepared respectively on the basis of the N- and C-terminal sequences of the $E_1$ protein gene, followed by primer annealing (i.e. double-stranded chain formation by hydrogen bonding) onto the $E_1$ protein gene in E. coli genomic DNA which has been made single-stranded by heat. After dNTP (where N is one of the deoxyribonucleotides A, G, C and T), AmpliTaq ® DNA polymerase (produced by Takara Shuzo Co., Ltd.), etc., are added to the DNA solution, the DNA primers are elongated along the $E_1$ protein gene as a template, to form DNA chains complementary to the template. The PCR cycle is repeated so that the $E_1$ protein gene only can be amplified and produced in a large amount.

The DNA fragments of the $E_1$ protein gene thus amplified are made blunt-ended with e.g. T4DNA polymerase (produced by Takara Shuzo Co., Ltd.) before insertion into e.g. a plasmid vector DNA.

The plasmid vector DNA used in the present invention is not particularly limited, which includes pUC119 DNA (produced by Takara Shuzo Co., Ltd.) etc., and specifically pBR322 type vectors e.g. pUTE100K' (described in Example 2) etc.

Such a plasmid vector DNA is digested with a restriction enzyme for generating blunt ends, i.e. HpaI (produced by Takara Shuzo Co., Ltd.) etc. at an enzyme concentration of 10–1000 U/ml at higher than 30° C., preferably 37° C., and for 1 hour, preferably 1–6 hours.

Then, the plasmid vector thus digested is mixed with the above DNA fragments of the $E_1$ protein gene, and the mixture is allowed to react in the presence of e.g. T4DNA ligase (produced by Boehringer Mannheim GmbH) at an enzyme concentration of 1–100 U/ml at a temperature of 4°–37° C., preferably 4°–16° C., and for 1 hour or more, preferably 6–24 hours.

The resultant recombinant DNA is transformed into *E. coli* K12, XL1-Blue, preferably JM109 (available from Takara Shuzo Co., Ltd.) etc. Transformation is effected by the method as described by D. M. Morrison [Methods in Enzymology, Vol. 68, pp. 326–331 (1979)].

The microorganism thus treated is then screened for a transformant possessing the $E_1$ protein activity of pyruvate dehydrogenase complex, i.e. *Escherichia coli* carrying the recombinant DNA in which a DNA fragment containing the $E_1$ protein gene is inserted into the vector DNA.

The bacterial strain thus selected is treated according to a method as described e.g. in Current Protocols in Molecular Biology, Vol. 1, Section 1 (1987), to give the novel recombinant DNA in pure form.

The $E_1$ protein-coding nucleotide sequence contained in the recombinant DNA partially differs from the known one: that is, it encodes variant $E_1$ protein wherein arginine at the 146-position is replaced by proline, and this mutation may be attributable to misreading of the elongation in the above PCR. For production of the variant $E_1$ protein, an *Escherichia coli* strain carrying said recombinant DNA is preferably cultured in liquid culture, although conventional solid culture can also be used.

Said bacterial strain is cultured in a medium in which one or more inorganic salts such as sodium chloride, potassium dihydrogen phosphate, potassium hydrogen phosphate, magnesium sulfate, ferric chloride, ferric sulfate, and manganese sulfate and, if necessary, sugars, vitamins, etc., are added to one or more nitrogen sources such as yeast extract, peptone, meat extract, corn steep liquor, and a bean or buckwheat immersion solution. The initial pH for the medium is preferably adjusted to pH 7–9. Culture is preferably conducted at 30°–42° C. preferably 37° C. or thereabout, and for 4–24 hours, preferably 6–8 hours, by spinner submerged culture under aeration, shaking culture, stationary culture, etc.

After the cultivation is finished, the variant $E_1$ protein can be recovered from the culture by a conventional means for enzyme recovery.

For extraction of the present enzyme, for example, the microorganism is disrupted by ultrasonic waves, ground, or lysed with lysozyme, or is autolysed in the presence of toluene etc. optionally under shaking. The solids in the resultant enzyme solution are removed by filtration, centrifugation, etc., if necessary followed by removal of nucleic acids with streptomycin sulfate, protamine sulfate, manganese sulfate, etc. The remaining enzyme solution is fractionated with ammonium sulfate, alcohol, acetone, etc., so that a crude enzyme is obtained as a precipitate.

A further purified enzyme preparation can be obtained from the above crude enzyme by a suitable combination of purification means, such as gel filtration on Sephadex, Ultrogel or Biogel; an absorption and elution method on ion-exchanger; electrolysis on polyacrylamide gel etc.; an absorption and elution method on hydroxyapatite; sedimentation by sucrose density-gradient centrifugation etc.; affinity chromatography; and fractionation by molecular sieve membrane, hollow fiber membrane, etc.

The variant $E_1$ protein thus purified has the same physicochemical properties as those of the published wild-type $E_1$ protein (for example, Methods in Enzymology, Vol. 9, pp. 247–265) except for the extremely high pyruvate dehydrogenase activity.

According to the present invention, therefore, there is provided the variant $E_1$ protein with one amino acid replaced by another amino acid, which possesses an extremely high $E_1$ activity as compared with the wild-type one. In addition, said variant $E_1$ protein can be efficiently obtained by culturing an *E. coli* strain carrying a recombinant DNA comprising the variant $E_1$ protein gene inserted therein.

EXAMPLES

The present invention is specifically described with reference to the following examples, which however are not intended to limit the scope of the invention.
(1) Preparation of genomic DNA from E. coli strain 1100

*E. coli* strain 1100 was inoculated onto 200 ml T-Y medium, pH 7.2{1% (W/V) Bacto-trypton [produced by Difco], 0.5% (W/V) Bacto-yeast extract [produced by Difco], 0.5% (W/V) NaCl} and cultured at 37° C. for 16 hours under shaking.

Then, the culture was centrifuged at 5000 r.p.m. for 10 min., to give 0.5 g wet microorganism, and its genomic DNA was obtained according to the method as described in Current Protocols in Molecular Biology, Vol. 1, Section 2 (1987).
(2) Cloning of the $E_1$ gene for the pyruvate dehydrogenase complex by the PCR technique For use as a template for PCR, 1 μg of the genomic DNA from *E. coli* strain 1100 was mixed with 0.2N NaOH, then denatured by heating at 70° C. for 10 min., and precipitated with ethanol to give a DNA template. Then, as single-stranded DNA primers for PCR, N- and C-terminal primers were synthesized respectively on the basis of the N- and C-terminal 30 residues of the $E_1$ gene by means of DNA synthesizer (manufactured by Applied Biosystems).

0.1 μg of the DNA template and 0.1 μM of each primer were subjected to PCR with a GeneAmp® PCR reagent kit (using AmpliTaq DNA polymerase) in DNA Thermal Cycler (manufactured by Perkin-Elmer Cetus Instruments). The reaction solution was then subjected to electrophoresis on 0.7% (W/V) agarose gel (produced by Takara Shuzo Co., Ltd.), and a band corresponding to $E_1$ gene fragments about 2.6–2.7 kb (kilo base pair) long was cut out and purified with GENE CLEAN II KIT® (produced by Funakoshi Co., Ltd.).

About 1 μg of the purified $E_1$ gene fragments was made blunt-ended with a DNA blunting kit (produced by Takara Shuzo Co., Ltd.) and was then ligated to HpaI-digested vector pUTE100K' (about 0.1 μg) at 16° C. for 16 hours.

According to the D. M. Morrison method [Methods in Enzymology, Vol. 68, pp. 326–331 (1979)], the above recombinant plasmid DNA obtained above was transformed into *E. coli* JM109 (obtained from Takara Shuzo Co., Ltd.) treated with calcium chloride. The resulting transformant was cultured at 37° C. for 24 hours on a T-Y agar plate medium containing 50 μg/ml ampicillin for screening of a transformant carrying the plasmid having the $E_1$ gene fragment operatively inserted into the vector DNA, so that *E. coli* JM109 (pACEE1K') was obtained.

The *E. coli* JM109 (pACEE1K') that is a transformant capable of producing the $E_1$ protein of pyruvate dehydrogenase complex has been deposited under FERM P-13547 with the National Institute of Bioscience and Human-Technology, Agency of Industrial Science and Technology, Japan.

The above vector pUTE100K' was prepared as follows:

The plasmid vector pBR322 DNA (produced by Takara Shuzo Co., Ltd.) was digested with EcoRI and NruI, then made blunt-ended with a DNA blunting kit (produced by Takara Shuzo Co., Ltd.), separated by agarose gel electrophoresis in a usual manner, and purified with GENECLEAN II, to give a DNA fragment about 3.4 kb long containing an origin of replication. This DNA fragment was cyclized with T4DNA ligase and then linearized by cleavage with EcoRI. Separately, a DNA sequence containing a HpaI restriction site and expression regulation regions such as a promoter, operator, ribosome-binding site, etc., derived from *E. coli* lactose operon etc. (see The Operon, p. 227, Cold Spring Harbor Laboratory, 1980) was synthesized with DNA Synthesizer Model 392 (manufactured by Applied Biosystems). This DNA fragment was ligated to the above EcoRI-digested fragment, thus giving rise to pUTE100.

The pUTE100 was digested with BglII, and a kanamycin resistant gene (produced by Pharmacia) digested at the BamHI site was linked thereto, whereby the expression vector pUTE100K' was prepared.

(3) Isolation of the recombinant plasmid pACEE1K' DNA 12.5 mg ampicillin was added to 250 ml T-Y medium, pH 7.2, composed of 1% (W/V) Bacto-trypton, 0.5% (W/V) Bacto-yeast extract and 0.5% (W/V) NaCl. *E. coli* JM109 (pACEE1K') was inoculated onto the medium and cultured at 37° C. for 20-24 hours under shaking.

Then, the culture was centrifuged for 10 min. at 5000 r.p.m. to give a wet microorganism, which was then suspended in 5 ml of 25 mM Tris-HCl buffer, pH 8.0, containing 50 mM glucose and 10 mM EDTA. After 25 mg lysozyme was added thereto, the suspension was allowed to stand for 5 min. at room temperature, to give a solution of lysed microorganism.

10 ml of 0.2N NaOH containing 1% (W/V) sodium dodecyl sulfate was added to the solution of lysed microorganism, and the mixture was allowed to stand at 0° C. for 10 min., to make the DNA denatured. Then, 7.5 ml of 5M potassium acetate-acetic acid buffer, pH 4.8, was added thereto and the mixture was allowed to stand at 0° C. for 10-30 min., so that the plasmid DNA only was regenerated. According to a conventional method, the solution was centrifuged for 20 min. at 9000 r.p.m. to give a supernatant which in turn was subjected to extraction with chloroform and then precipitated with ethanol.

The precipitate was dried under reduced pressure and then dissolved in 6 ml of 10 mM Tris-HCl buffer, pH 7.5, containing 1 mM EDTA, followed by addition of 6 g cesium chloride and 0.3 ml of 10 mg/ml ethidium bromide. For isolation of the recombinant plasmid pACEE1K' DNA, the sample solution was subjected to equilibrium density-gradient centrifugation for 20 hours at 50000 r.p.m. by means of a ultracentrifugate. After ethidium bromide was removed by extraction with n-butanol, the sample solution was dialyzed against 10 mM Tris-HCl buffer (pH 7.5) containing 1 mM EDTA, to give 100 μg of purified recombinant plasmid pACEE1K' DNA.

(4) Analysis of the nucleotide sequence of the $E_1$ gene of pyruvate dehydrogenase complex For analysis of the nucleotide sequence from the N-terminal of the $E_1$ gene, the $E_1$ gene-inserted plasmid pACEE1K' obtained in above item (3) was cleaved at the various restriction enzyme cleave sites in the $E_1$ gene. The plasmid pACEE1K' was digested with various restriction enzymes to form a variety of DNA fragments which were then cloned into a multicloning site of plasmid pUC118 or pUC119 DNA (each obtained from Takara Shuzo Co., Ltd.). Each recombinant plasmid DNA thus obtained was transformed into *E. coli* JM109 (obtained from Takara Shuzo Co. Ltd.).

In the above process, linkage by T4DNA ligase, transformation and isolation of the DNA fragments by agarose gel electrophoresis were conducted according to the method as described in item (2) above.

The transformant thus obtained was infected with helper phage M13K07 (produced by Takara Shuzo Co., Ltd.) and then treated according to the Messing method (Methods in Enzymology, Vol. 101, pp. 20-78 (1983)), whereby a single-stranded DNA was prepared.

For sequencing, the single-stranded DNA was subjected to the above-mentioned Messing method using Dye Primer Taq Sequencing Kit (produced by Applied Biosystems). The nucleotide fragments were separated by gel electrophoresis on 6% polyacrylamide gel (produced by National Diagnostics) containing 50% (W/V) urea and analyzed by DNA Sequencer 370A (manufactured by Applied Biosystems).

The entire nucleotide sequence of the E1 gene for the pyruvate dehydrogenase complex is set forth in SEQ ID No:2 and the amino acid sequence of the polypeptide encoded by said gene is set forth in SEQ ID. No:1:

The present nucleotide sequence differs from the already reported sequence of the $E_1$ gene from *E. coli* strain K12 in that G (guanine) at the 437-position is replaced by C (cytosine) in the nucleotide sequence, resulting in the production of the variant $E_1$ protein wherein arginine at the 146-position is replaced by proline.

(5) Preparation of the $E_1$ protein with the same amino acid sequence as the published sequence by site-specific mutation Site-specific mutation was carried out so that a recombinant producing the same wild-type $E_1$ protein as the published one was obtained from the above recombinant having the ability to produce the variant $E_1$ protein and carrying the plasmid pACEE1K' containing the variant $E_1$ gene. That is, a DNA fragment of the $E_1$ gene mutated at the 437-position was excised, with a suitable restriction enzyme, from the plasmid pACEE1K' obtained in above item (3), followed by ligation to pUC119 DNA at a multicloning site (produced by Takara Shuzo Co., Ltd.). The resulting recombinant DNA was transformed into *E. coli* XL.1-Blue (available from Takara Shuzo Co., Ltd.). The transformant thus obtained was infected with helper phage M13K07 (produced by Takara Shuzo Co., Ltd.), and its single-stranded DNA was prepared according to the Messing method (Methods in Enzymology, Vol. 101, pp. 20–78 (1983)). As a single-stranded DNA primer for site-specific mutation, a primer consisting of 34 residues of the $E_1$ gene (containing G (in the wild-type) but not C (in the variant) at the 437-position) was synthesized with a DNA synthesizer (manufactured by Applied Biosystems). The single-stranded DNA and primer thus obtained were used for site-specific mutation with Oligonucleotide-Directed In Vitro Mutagenesis System (produced by Amersham). A DNA fragment containing G at the 437-position was excised from the resulting plasmid with a suitable restriction enzyme. Subsequently, said DNA fragment was inserted into the plasmid pACEE1K' in such a manner that the corresponding original fragment is replaced by said DNA fragment, whereby a recombinant capable of producing the E1 protein of the wild-type amino acid sequence was obtained.

(6) Comparison in activity between variant $E_1$ protein and wild-type $E_1$ protein Each 150 ml Erlenmeyer flask was charged with 10 ml of a medium composed of 1% (W/V) Bacto-trypton, 0.5% (W/V) Bacto-yeast extract, 1 mM isopropyl-$\beta$-D-thiogalactoside and 0.5 % (W/V) NaCl, and the medium was sterilized under high pressure. Each culture, 200 $\mu$l, from transformants capable of producing the variant $E_1$ protein and those producing wild-type $E_1$ protein, pre-cultured at 37° C. for 14 hours in a culture medium with the same composition as above mentioned, was transferred into the medium prepared above and cultured under shaking at 37° C. for 8 hours. Then, 3 ml of the culture was centrifuged at 4000 r.p.m. for 10 min. and the resulting wet microorganism was suspended in 3 ml of 0.1M phosphate buffer, pH 8.0 and then disrupted by sonication in a usual manner and centrifuged for 5 min. at 12000 r.p.m., to give 3 ml of each of variant and wild-type crude enzyme solutions.

Separately, each strain producing the enzymes $E_2$ and $E_3$ of the pyruvate dehydrogenase complex was cultured, and each crude enzyme, 3 ml, was obtained in the same manner as $E_1$. Then, enough amounts of $E_2$ and $E_3$ were added to each of crude variant and wild-type $E_1$ enzymes. As a result, the activities of the variant and wild-type enzymes were 0.9 U/ml and 0.15 U/ml, respectively.

It is understood from the data that the enzyme activity of the variant $E_1$ protein is about 6 times higher than that of the wild-type $E_1$ protein.

---

What is claimed is:

1. An isolated gene coding for the amino acid sequence of variant E₁ protein of *E. coli* pyruvate dehydrogenase complex in which arginine at the 146-position is replaced by proline in the amino acid sequence of wild-type E₁ protein of *E. coli* pyruvate dehydrogenase complex.

2. A recombinant DNA comprising the gene for the variant $E_1$ protein of *E. coli* pyruvate dehydrogenase complex of claim 1 inserted into a vector DNA.

3. A process for producing variant $E_1$ protein of *E. coli* pyruvate dehydrogenase complex, comprising culturing a microorganism of genus Escherichia carrying the recombinant DNA of claim 2 and recovering the variant $E_1$ protein of *E. coli* pyruvate dehydrogenase complex from the culture.

4. Variant $E_1$ protein of *E. coli* pyruvate dehydrogenase complex in which arginine at the 146-position is replaced by proline in the amino acid sequence of wild-type $E_1$ protein of *E. coli* pyruvate dehydrogenase.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 887 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Met  Ser  Glu  Arg  Phe  Pro  Asn  Asp  Val  Asp  Pro  Ile  Glu  Thr  Arg  Asp
 1              5                        10                       15

Trp  Leu  Gln  Ala  Ile  Glu  Ser  Val  Ile  Arg  Glu  Glu  Gly  Val  Glu  Arg
               20                       25                  30

Ala  Gln  Tyr  Leu  Ile  Asp  Gln  Leu  Leu  Ala  Glu  Ala  Arg  Lys  Gly  Gly
          35                  40                       45

Val  Asn  Val  Ala  Ala  Gly  Thr  Gly  Ile  Ser  Asn  Tyr  Ile  Asn  Thr  Ile
     50                       55                  60

Pro  Val  Glu  Glu  Gln  Pro  Glu  Tyr  Pro  Gly  Asn  Leu  Glu  Leu  Glu  Arg
 65                      70                       75                       80

Arg  Ile  Arg  Ser  Ala  Ile  Arg  Trp  Asn  Ala  Ile  Met  Thr  Val  Leu  Arg
                    85                       90                       95

Ala  Ser  Lys  Lys  Asp  Leu  Glu  Leu  Gly  Gly  His  Met  Ala  Ser  Phe  Gln
              100                      105                 110

Ser  Ser  Ala  Thr  Ile  Tyr  Asp  Val  Cys  Phe  Asn  His  Phe  Phe  Arg  Ala
              115                      120                 125

Arg  Asn  Glu  Gln  Asp  Gly  Gly  Asp  Leu  Val  Tyr  Phe  Gln  Gly  His  Ile
         130                 135                      140

Ser  Pro  Gly  Val  Tyr  Ala  Arg  Ala  Phe  Leu  Glu  Gly  Arg  Leu  Thr  Gln
145                          150                      155                 160

Glu  Gln  Leu  Asp  Asn  Phe  Arg  Gln  Glu  Val  His  Gly  Asn  Gly  Leu  Ser
```

-continued

|  |  |  | 165 |  |  |  | 170 |  |  |  | 175 |  |  |
|---|---|---|---|---|---|---|---|---|---|---|---|---|---|
| Ser | Tyr | Pro | His<br>180 | Pro | Lys | Leu | Met | Pro<br>185 | Glu | Phe | Trp | Gln<br>190 | Phe | Pro | Thr |
| Val | Ser | Met<br>195 | Gly | Leu | Gly | Pro | Ile<br>200 | Gly | Ala | Ile | Tyr | Gln<br>205 | Ala | Lys | Phe |
| Leu | Lys<br>210 | Tyr | Leu | Glu | His | Arg<br>215 | Gly | Leu | Lys | Asp | Thr<br>220 | Ser | Lys | Gln | Thr |
| Val<br>225 | Tyr | Ala | Phe | Leu | Gly<br>230 | Asp | Gly | Glu | Met | Asp<br>235 | Glu | Pro | Glu | Ser | Lys<br>240 |
| Gly | Ala | Ile | Thr | Ile<br>245 | Ala | Thr | Arg | Glu | Lys<br>250 | Leu | Asp | Asn | Leu | Val<br>255 | Phe |
| Val | Ile | Asn | Cys<br>260 | Asn | Leu | Gln | Arg | Leu<br>265 | Asp | Gly | Pro | Val | Thr<br>270 | Gly | Asn |
| Gly | Lys | Ile<br>275 | Ile | Asn | Glu | Leu | Glu<br>280 | Gly | Ile | Phe | Glu | Gly<br>285 | Ala | Gly | Trp |
| Asn | Val<br>290 | Ile | Lys | Val | Met | Trp<br>295 | Gly | Ser | Arg | Trp | Asp<br>300 | Glu | Leu | Leu | Arg |
| Lys<br>305 | Asp | Thr | Ser | Gly | Lys<br>310 | Leu | Ile | Gln | Leu | Met<br>315 | Asn | Glu | Thr | Val | Asp<br>320 |
| Gly | Asp | Tyr | Gln | Thr<br>325 | Phe | Lys | Ser | Lys | Asp<br>330 | Gly | Ala | Tyr | Val | Arg<br>335 | Glu |
| His | Phe | Phe | Gly<br>340 | Lys | Tyr | Pro | Glu | Thr<br>345 | Ala | Ala | Leu | Val | Ala<br>350 | Asp | Trp |
| Thr | Asp | Glu<br>355 | Gln | Ile | Trp | Ala | Leu<br>360 | Asn | Arg | Gly | Gly | His<br>365 | Asp | Pro | Lys |
| Lys | Ile<br>370 | Tyr | Ala | Ala | Phe | Lys<br>375 | Lys | Ala | Gln | Glu | Thr<br>380 | Lys | Gly | Lys | Ala |
| Thr<br>385 | Val | Ile | Leu | Ala | His<br>390 | Thr | Ile | Lys | Gly | Tyr<br>395 | Gly | Met | Gly | Asp | Ala<br>400 |
| Ala | Glu | Gly | Lys | Asn<br>405 | Ile | Ala | His | Gln | Val<br>410 | Lys | Lys | Met | Asn | Met<br>415 | Asp |
| Gly | Val | Arg | His<br>420 | Ile | Arg | Asp | Arg | Phe<br>425 | Asn | Val | Pro | Val | Ser<br>430 | Asp | Ala |
| Asp | Ile | Glu<br>435 | Lys | Leu | Pro | Tyr | Ile<br>440 | Thr | Phe | Pro | Glu | Gly<br>445 | Ser | Glu | Glu |
| His | Thr<br>450 | Tyr | Leu | His | Ala | Gln<br>455 | Arg | Gln | Lys | Leu | His<br>460 | Gly | Tyr | Leu | Pro |
| Ser<br>465 | Arg | Gln | Pro | Asn | Phe<br>470 | Thr | Glu | Lys | Leu | Glu<br>475 | Leu | Pro | Ser | Leu | Gln<br>480 |
| Asp | Phe | Gly | Ala | Leu<br>485 | Leu | Glu | Glu | Gln | Ser<br>490 | Lys | Glu | Ile | Ser | Thr<br>495 | Thr |
| Ile | Ala | Phe | Val<br>500 | Arg | Ala | Leu | Asn | Val<br>505 | Met | Leu | Lys | Asn | Lys<br>510 | Ser | Ile |
| Lys | Asp | Arg<br>515 | Leu | Val | Pro | Ile | Ile<br>520 | Ala | Asp | Glu | Ala | Arg<br>525 | Thr | Phe | Gly |
| Met | Glu<br>530 | Gly | Leu | Phe | Arg | Gln<br>535 | Ile | Gly | Ile | Tyr | Ser<br>540 | Pro | Asn | Gly | Gln |
| Gln | Tyr | Thr<br>545 | Pro | Gln | Asp | Arg<br>550 | Glu | Gln | Val | Ala | Tyr<br>555 | Tyr | Lys | Glu | Asp<br>560 |
| Glu | Lys | Gly | Gln | Ile<br>565 | Leu | Gln | Glu | Gly | Ile<br>570 | Asn | Glu | Leu | Gly | Ala<br>575 | Gly |
| Cys | Ser | Trp | Leu | Ala<br>580 | Ala | Ala | Thr | Ser<br>585 | Tyr | Ser | Thr | Asn | Asn<br>590 | Leu | Pro |
| Met | Ile | Pro<br>595 | Phe | Tyr | Ile | Tyr | Tyr<br>600 | Ser | Met | Phe | Gly | Phe<br>605 | Gln | Arg | Ile |

| | | | | | | | | | | | | | | |
|---|---|---|---|---|---|---|---|---|---|---|---|---|---|---|
| Gly | Asp | Leu | Cys | Trp | Ala | Ala | Gly | Asp | Gln | Gln | Ala | Arg | Gly | Phe | Leu |
| | 610 | | | | 615 | | | | 620 | | | | | | |
| Ile | Gly | Gly | Thr | Ser | Gly | Arg | Thr | Thr | Leu | Asn | Gly | Glu | Gly | Leu | Gln |
| 625 | | | | | 630 | | | | 635 | | | | | | 640 |
| His | Glu | Asp | Gly | His | Ser | His | Ile | Gln | Ser | Leu | Thr | Ile | Pro | Asn | Cys |
| | | | | 645 | | | | | 650 | | | | | 655 | |
| Ile | Ser | Tyr | Asp | Pro | Ala | Tyr | Ala | Tyr | Glu | Val | Ala | Val | Ile | Met | His |
| | | | 660 | | | | 665 | | | | | | 670 | | |
| Asp | Gly | Leu | Glu | Arg | Met | Tyr | Gly | Glu | Lys | Gln | Glu | Asn | Val | Tyr | Tyr |
| | | | 675 | | | | 680 | | | | | 685 | | | |
| Tyr | Ile | Thr | Thr | Leu | Asn | Glu | Asn | Tyr | His | Met | Pro | Ala | Met | Pro | Glu |
| | 690 | | | | 695 | | | | | 700 | | | | | |
| Gly | Ala | Glu | Glu | Gly | Ile | Arg | Lys | Gly | Ile | Tyr | Lys | Leu | Glu | Thr | Ile |
| 705 | | | | | 710 | | | | 715 | | | | | | 720 |
| Glu | Gly | Ser | Lys | Gly | Lys | Val | Gln | Leu | Leu | Gly | Ser | Gly | Ser | Ile | Leu |
| | | | | 725 | | | | | 730 | | | | | 735 | |
| Arg | His | Val | Arg | Glu | Ala | Ala | Glu | Ile | Leu | Ala | Lys | Asp | Tyr | Gly | Val |
| | | | 740 | | | | | 745 | | | | | 750 | | |
| Gly | Ser | Asp | Val | Tyr | Ser | Val | Thr | Ser | Phe | Thr | Glu | Leu | Ala | Arg | Asp |
| | | 755 | | | | | 760 | | | | | 765 | | | |
| Gly | Gln | Asp | Cys | Glu | Arg | Trp | Asn | Met | Leu | His | Pro | Leu | Glu | Thr | Pro |
| | 770 | | | | | 775 | | | | | 780 | | | | |
| Arg | Val | Pro | Tyr | Ile | Ala | Gln | Val | Met | Asn | Asp | Ala | Pro | Ala | Val | Ala |
| 785 | | | | | 790 | | | | | 795 | | | | | 800 |
| Ser | Thr | Asp | Tyr | Met | Lys | Leu | Phe | Ala | Glu | Gln | Val | Arg | Thr | Tyr | Val |
| | | | | 805 | | | | | 810 | | | | | 815 | |
| Pro | Ala | Asp | Asp | Tyr | Arg | Val | Leu | Gly | Thr | Asp | Gly | Phe | Gly | Arg | Ser |
| | | | 820 | | | | | 825 | | | | | 830 | | |
| Asp | Ser | Arg | Glu | Asn | Leu | Arg | His | His | Phe | Glu | Val | Asp | Ala | Ser | Tyr |
| | | 835 | | | | | 840 | | | | | 845 | | | |
| Val | Val | Val | Ala | Ala | Leu | Gly | Glu | Leu | Ala | Lys | Arg | Gly | Glu | Ile | Asp |
| | 850 | | | | | 855 | | | | | 860 | | | | |
| Lys | Lys | Val | Val | Ala | Asp | Ala | Ile | Ala | Lys | Phe | Asn | Ile | Asp | Ala | Asp |
| 865 | | | | | 870 | | | | | 875 | | | | | 880 |
| Lys | Val | Asn | Pro | Arg | Leu | Ala | | | | | | | | | |
| | | | | 885 | | | | | | | | | | | |

(2) INFORMATION FOR SEQ ID NO:2:

( i ) SEQUENCE CHARACTERISTICS:
        ( A ) LENGTH: 2664 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

```
ATGTCAGAAC GTTTCCCAAA TGACGTGGAT CCGATCGAAA CTCGCGACTG GCTCCAGGCG      60

ATCGAATCGG TCATCCGTGA AGAAGGTGTT GAGCGTGCTC AGTATCTGAT CGACCAACTG     120

CTTGCTGAAG CCCGCAAAGG CGGTGTAAAC GTAGCCGCAG GCACAGGTAT CAGCAACTAC     180

ATCAACACCA TCCCCGTTGA GAACAACCG GAGTATCCGG TAATCTGGA ACTGGAACGC       240

CGTATTCGTT CAGCTATCCG CTGGAACGCC ATCATGACGG TGCTGCGTGC GTCGAAAAA     300

GACCTCGAAC TGGGCGGCCA TATGGCGTCC TTCCAGTCTT CCGCAACCAT TTATGATGTG     360

TGCTTTAACC ACTTCTTCCG TGCACGCAAC GAGCAGGATG GCGGCGACCT GGTTTACTTC     420
```

| | | | | | |
|---|---|---|---|---|---|
| CAGGGCCACA | TCTCCCCGGG | CGTGTACGCT | CGTGCTTTCC | TGGAAGGTCG | TCTGACTCAG | 480
| GAGCAGCTGG | ATAACTTCCG | TCAGGAAGTT | CACGGCAATG | GCCTCTCTTC | CTATCCGCAC | 540
| CCGAAACTGA | TGCCGGAATT | CTGGCAGTTC | CCGACCGTAT | CTATGGGTCT | GGGTCCGATT | 600
| GGTGCTATTT | ACCAGGCTAA | ATTCCTGAAA | TATCTGGAAC | ACCGTGGCCT | GAAAGATACC | 660
| TCTAAACAAA | CCGTTTACGC | GTTCCTCGGT | GACGGTGAAA | TGGACGAACC | GGAATCCAAA | 720
| GGTGCGATCA | CCATCGCTAC | CCGTGAAAAA | CTGGATAACC | TGGTCTTCGT | TATCAACTGT | 780
| AACCTGCAGC | GTCTTGACGG | CCCGGTCACC | GGTAACGGCA | AGATCATCAA | CGAACTGGAA | 840
| GGCATCTTCG | AAGGTGCTGG | CTGGAACGTG | ATCAAAGTGA | TGTGGGGTAG | CCGTTGGGAT | 900
| GAACTGCTGC | GTAAGGATAC | CAGCGGTAAA | CTGATCCAGC | TGATGAACGA | AACCGTTGAC | 960
| GGCGACTACC | AGACCTTCAA | ATCGAAAGAT | GGTGCGTACG | TTCGTGAACA | CTTCTTCGGT | 1020
| AAATATCCTG | AAACCGCAGC | ACTGGTTGCA | GACTGGACTG | ACGAGCAGAT | CTGGGCACTG | 1080
| AACCGTGGTG | GTCACGATCC | GAAGAAAATC | TACGCTGCAT | TCAAGAAAGC | GCAGGAAACC | 1140
| AAAGGCAAAG | CGACAGTAAT | CCTTGCTCAT | ACCATTAAAG | GTTACGGCAT | GGGCGACGCG | 1200
| GCTGAAGGTA | AAAACATCGC | GCACCAGGTT | AAGAAAATGA | ACATGGACGG | TGTGCGTCAT | 1260
| ATCCGCGACC | GTTTCAATGT | GCCGGTGTCT | GATGCAGATA | TCGAAAAACT | GCCGTACATC | 1320
| ACCTTCCCGG | AAGGTTCTGA | AGAGCATACC | TATCTGCACG | CTCAGCGTCA | GAAACTGCAC | 1380
| GGTTATCTGC | CAAGCCGTCA | GCCGAACTTC | ACCGAGAAGC | TTGAGCTGCC | GAGCCTGCAA | 1440
| GACTTCGGCG | CGCTGTTGGA | AGAGCAGAGC | AAAGAGATCT | CTACCACTAT | CGCTTTCGTT | 1500
| CGTGCTCTGA | ACGTGATGCT | GAAGAACAAG | TCGATCAAAG | ATCGTCTGGT | ACCGATCATC | 1560
| GCCGACGAAG | CGCGTACTTT | CGGTATGGAA | GGTCTGTTCC | GTCAGATTGG | TATTTACAGC | 1620
| CCGAACGGTC | AGCAGTACAC | CCCGCAGGAC | CGCGAGCAGG | TTGCTTACTA | TAAAGAAGAC | 1680
| GAGAAGGTC | AGATTCTGCA | GGAAGGGATC | AACGAGCTGG | CGCAGGTTG | TTCCTGGCTG | 1740
| GCAGCGGCGA | CCTCTTACAG | CACCAACAAT | CTGCCGATGA | TCCCGTTCTA | CATCTATTAC | 1800
| TCGATGTTCG | GCTTCCAGCG | TATTGGCGAT | CTGTGCTGGG | CGGCTGGCGA | CCAGCAAGCG | 1860
| CGTGGCTTCC | TGATCGGCGG | TACTTCCGGT | CGTACCACCC | TGAACGGCGA | AGGTCTGCAG | 1920
| CACGAAGATG | GTCACAGCCA | CATTCAGTCG | CTGACTATCC | CGAACTGTAT | CTCTTACGAC | 1980
| CCGGCTTACG | CTTACGAAGT | TGCTGTCATC | ATGCATGACG | GTCTGGAGCG | TATGTACGGT | 2040
| GAAAAACAAG | AGAACGTTTA | CTACTACATC | ACTACGCTGA | ACGAAAACTA | CCACATGCCG | 2100
| GCAATGCCGG | AAGGTGCTGA | GGAAGGTATC | CGTAAAGGTA | TCTACAAACT | CGAAACTATT | 2160
| GAAGGTAGCA | AAGGTAAAGT | TCAGCTGCTC | GGCTCCGGTT | CTATCCTGCG | TCACGTCCGT | 2220
| GAAGCAGCTG | AGATCCTGGC | GAAAGATTAC | GGCGTAGGTT | CTGACGTTTA | TAGCGTGACC | 2280
| TCCTTCACCG | AGCTGGCGCG | TGATGGTCAG | GATTGTGAAC | GCTGGAACAT | GCTGCACCCG | 2340
| CTGGAAACTC | CGCGCGTTCC | GTATATCGCT | CAGGTGATGA | ACGACGCTCC | GGCAGTGGCA | 2400
| TCTACCGACT | ATATGAAACT | GTTCGCTGAG | CAGGTCCGTA | CTTACGTACC | GGCTGACGAC | 2460
| TACCGCGTAC | TGGGTACTGA | TGGCTTCGGT | CGTTCCGACA | GCCGTGAGAA | CCTGCGTCAC | 2520
| CACTTCGAAG | TTGATGCTTC | TTATGTCGTG | GTTGCGGCGC | TGGGCGAACT | GGCTAAACGT | 2580
| GGCGAAATCG | ATAAGAAAGT | GGTTGCTGAC | GCAATCGCCA | AATTCAACAT | CGATGCAGAT | 2640
| AAAGTTAACC | CGCGTCTGGC | GTAA | | | | 2664